United States Patent

Peglion et al.

[11] Patent Number: 6,107,345
[45] Date of Patent: Aug. 22, 2000

[54] BENZOCYCLOBUTANE COMPOUNDS

[75] Inventors: Jean-Louis Peglion, Le Vesinet; Aimée Dessinges, Rueil Malmaison, both of France; Jean-Christophe Harmange, Andover, Mass.; Mark Millan; Adrian Newman-Tancredi, both of Le Pecq, France; Mauricette Brocco, Paris, France

[73] Assignee: Adir et Compagnie, Courbevoie, France

[21] Appl. No.: 09/261,803

[22] Filed: Mar. 3, 1999

[30] Foreign Application Priority Data

Apr. 3, 1998 [FR] France ................................. 98 02585

[51] Int. Cl.[7] .................... A61K 31/133; C07C 215/42
[52] U.S. Cl. ...................... 514/650; 514/319; 514/374; 514/399; 514/430; 514/432; 514/449; 514/451; 514/517; 514/657; 546/205; 546/237; 546/331.1; 548/28; 548/88; 548/419; 548/423; 548/510; 548/57; 564/339; 564/428
[58] Field of Search ..................... 564/339, 428; 558/57; 549/28, 88, 419, 423, 510; 548/237, 331.1; 546/205; 514/319, 374, 399, 430, 432, 449, 451, 517, 650, 657

[56] References Cited

U.S. PATENT DOCUMENTS 5,189,045 2/1993 Peglion et al. .................... 514/319
5,214,055 5/1993 Peglion et al. .................... 514/320

*Primary Examiner*—Richard L. Raymond
*Attorney, Agent, or Firm*—The firm of Gordon W. Hueschen

[57] ABSTRACT

A compound of formula (I):

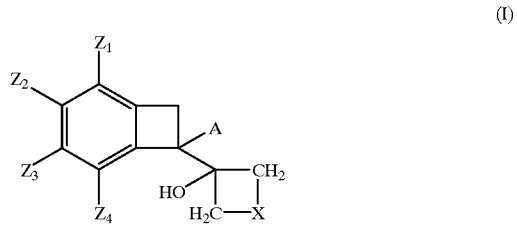

wherein:

$Z_1$, $Z_2$, $Z_3$, $Z_4$, which may be identical or different, represent a group as defined in the description, X represents oxygen, $S(O)_p$, $—(CH_2)_n—$ or $—CH_2—Y—CH_2—$ wherein p, n and Y are as defined in the description, A represents

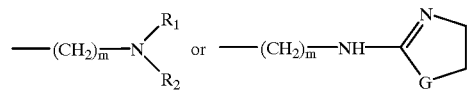

wherein m, $R_1$, $R_2$ and G are as defined in the description, their isomers and addition salts thereof with a pharmaceutically-acceptable acid, and medicinal products containing the same are useful in the treatment of diseases like depression, panic attacks, obsessive compulsive disorders, phobias, impulsive disorders, drug abuse or anxiety.

18 Claims, No Drawings

BENZOCYCLOBUTANE COMPOUNDS

FIELD OF THE INVENTION

The present invention relates to new benzocyclobutane compounds, to a process for their preparation and to pharmaceutical compositions containing them.

The compounds of the present invention act as powerful inhibitors of serotonin reuptake and as inhibitors of noradrenaline reuptake.

They can accordingly be used therapeutically in the treatment of depression, panic attacks, obsessive compulsive disorders, phobias, impulsive disorders, drug abuse and anxiety.

Indeed, in the forced swimming test in the mouse (Porsolt et. al., *Arch. Intern. Pharmacodyn. Therap.*, 1977, 229, p. 327) and in the suspension-by-the-tail test in the mouse (Stéru et al., *Psychopharmacology*, 1985, 85, 367–370), the compounds of the present invention demonstrate excellent activity compared with the reference compounds, such as fluoxetine.

The closest prior art to the present invention is illustrated in Patent EP 0 457 686 B1 which relates to $5HT_{1A}$ receptor antagonists that can be used in the treatment of pain, stress, migraine, anxiety, depression and schizophrenia, the structure of which could not, however, lead to that of the compounds of the present invention.

DETAILED DESCRIPTION OF THE INVENTION

More specifically, the present invention relates to compounds of formula (I):

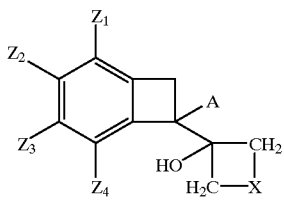

(I)

wherein:

$Z_1$, $Z_2$, $Z_3$, $Z_4$, which may be the same or different, each represent a hydrogen atom, a halogen atom, a linear or branched ($C_1$–$C_6$)alkyl group, a linear or branched ($C_2$–$C_6$)-alkenyl group, a linear or branched ($C_2$–$C_6$)alkynyl group, a [($C_3$–$C_8$)-cycloalkyl]-($C_1$–$C_6$)alkyl group, the alkyl moiety of which is linear or branched, a hydroxy group, a linear or branched ($C_1$–$C_6$)alkoxy group, a benzyloxy-($C_2$–$C_6$)-alkenoxy group, the alkenyl moiety of which is linear or branched, a linear or branched ($C_2$–$C_6$)alkynoxy group, a cyano group, a trifluoromethyl group, a trifluoromethoxy group, a nitro group, a group of formula $-OSO_2CF_3$, $OSO_2CH_3$, $-NHCOCH_3$, $-NHCOCF_3$, $-NHSO_2CH_3$,

or a group of formula

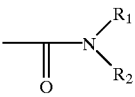

wherein $R_1$ and $R_2$, which may be the same or different, each represent a hydrogen atom, a linear or branched ($C_1$–$C_6$) alkyl group, a linear or branched ($C_2$–$C_6$)alkenyl group, a linear or branched ($C_2$–$C_6$)alkynyl group, an aryl-($C_1$–$C_6$) alkyl group, the alkyl moiety of which is linear or branched, or a [($C_3$–$C_8$)cycloalkyl]-($C_1$–$C_6$)alkyl group, the alkyl moiety of which is linear or branched, X represents:

an oxygen atom, a group of formula $S(O)_p$ wherein p represents an integer from 0 to 2 inclusive, a group of formula $-(CH_2)_n$ wherein n represents an integer from 1 to 4 inclusive, or a group of formula $-CH_2-Y-CH_2-$ wherein Y represents an oxygen atom, a selenium atom, a group

wherein p is as defined above,

or

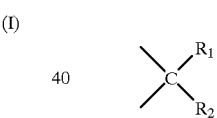

wherein $R_1$ and $R_2$ are as defined above,

A represents a group of formula:

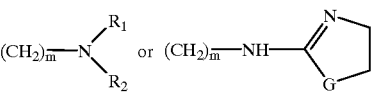

wherein $R_1$ and $R_2$ are as defined above, m represents an integer from 1 to 6 inclusive, and G represents an oxygen atom or the group NH, their isomers and addition salts thereof with a pharmaceutically acceptable acid.

The term "aryl group" is understood to mean a phenyl, naphthyl, indene, tetrahydronaphthyl, dihydronaphthyl or dihydroindene group, each of those groups being optionally substituted by one or more identical or different groups selected from halogen atoms, linear or branched ($C_1$–$C_6$) alkyl groups, hydroxy group and linear or branched ($C_1$–$C_6$) alkoxy groups.

Among the pharmaceutically acceptable acids there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methane-sulphonic acid, comphoric acid, etc.

The preferred group A of the compounds of the invention is the group of formula

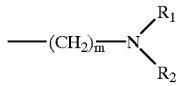

wherein m, $R_1$ and $R_2$ are as defined above.

According to an advantageous embodiment of the invention, the preferred compounds are the compounds of formula (K) wherein X represents a group of formula $-(CH_2)_n-$ wherein n is as defined for formula (I).

In an especially advantageous manner, the preferred compounds of the invention are the compounds of formula (I) wherein:

A represents a group of formula

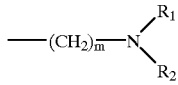

wherein $R_1$ and $R_2$ are as defined above and m is 1, and X represents a group of formula $-(CH_2)_n-$ wherein n is 3.

According to another embodiment of the invention, the preferred compounds are the compounds of formula (I) wherein X represents a group of formula $-CH_2-Y-CH_2$ wherein Y is as defined for formula (I).

The preferred groups $Z_1$, $Z_2$, $Z_3$ and $Z_4$, which may be the same or different, are the groups whose meanings are selected from a hydrogen atom, a halogen atoms, a hydroxy group, a linear or branched $(C_1-C_6)$alkoxy group, a linear or branched $(C_1-C_6)$alkyl group, a trifluoromethyl group and a trifluoromethoxy group.

The preferred compounds of the invention are the compounds of formula (I) corresponding to:

1-(N,N-dimethylaminomethyl)-1-(1-hydroxycyclohex-1-yl)-5-methoxybenzocyclobutane, 1-(N,N-dimethylaminomethyl)-1-(1-hydroxycyclohex-1-yl)-4-methoxybenzocyclobutane, and (−)-1-(N,N-dimethylaminomethyl)-1-(1-hydroxycyclohex-1-yl)-5-methoxybenzocyclobutane.

The isomers and addition salts with a pharmaceutically acceptable acid of the preferred compounds form an integral part of the invention.

The present invention relates to a process for the preparation of compounds of formula (I), characterised in that there is used as starting material:

a compound of formula (II):

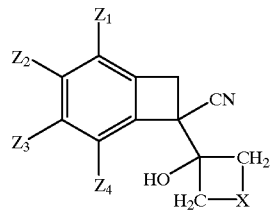

(II)

wherein $Z_1$, $Z_2$, $Z_3$, $Z_4$ and X are as defined for formula (I), which is treated with a hydride in ether or in tetrahydrofuran, to yield the compounds of formula (I/a), a particular case of the compounds of formula (I):

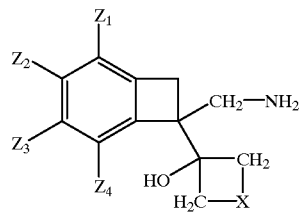

(I/a)

wherein $Z_1$, $Z_2$, $Z_3$, $Z_4$ and X are as defined above, which compounds of formula (I/a) are substituted using conventional methods of organic chemistry, such as, for example:

reductive amination starting from the corresponding aldehydes or ketones, in the presence of sodium cyanoborohydride or sodium triacetoxyborohydride, or nucleophilic substitution of compounds of formula (III):

$R'_1 Z$ (III)

wherein $R'_1$ has the meaning given above for $R_1$ with the exception of the meaning hydrogen, and Z is a leaving group such as, for example, I, Br, Cl,

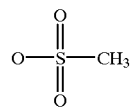

or

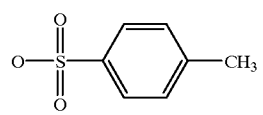

to yield the secondary amines of formula (I/b), a particular case of the compounds of formula (I):

(I/b)

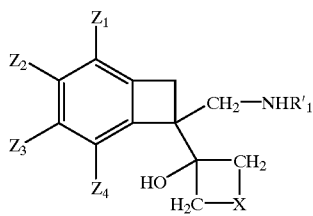

wherein $Z_1$, $Z_2$, $Z_3$, $Z_4$, X and $R'_1$ are as defined above, which compounds of formula (I/b) are again substituted using the same methods as those described above to yield the tertiary amines of formula (I/c), a particular case of the compounds (I):

(I/c)

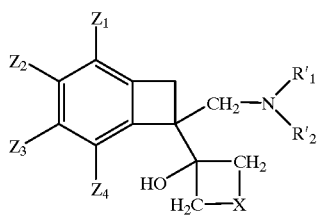

wherein $Z_1$, $Z_2$, $Z_3$, $Z_4$ and X are as defined above and $R'_1$ and $R'_2$ have the meanings given above for $R_1$ and $R_2$, respectively, with the exception of the meaning hydrogen, with the proviso that when $R'_1$ and $R'_2$ are the same, each being other than hydrogen, the tertiary amines of formula (I/c) are obtained directly from the amine (I/a) without having to isolate the secondary amine (I/b), or a compound of formula (IV):

(IV)

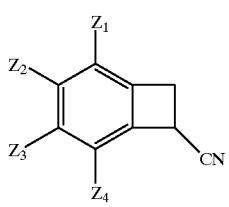

wherein $Z_1$, $Z_2$, $Z_3$, $Z_4$ are as defined for formula (I), which is substituted, in the presence of a strong base, by an amine of formula (V):

(V)

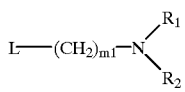

wherein $R_1$ and $R_2$ are as defined for formula (I), m1 is an integer from 2 to 6 inclusive and L represents a leaving group, such as a halogen atom, a mesylate, tosylate or trifluoromethanesulphonate group, etc., to yield compounds of formula (VI):

(VI)

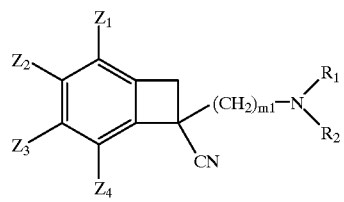

wherein $Z_1$, $Z_2$, $Z_3$, $Z_4$, $R_1$, $R_2$ and m1 are as defined above, which compounds of formula (VI) are treated under conditions of alcoholic acid hydrolysis in the presence of a compound of formula (VII):

$$G\text{—}OH \quad (VII)$$

wherein G represents a linear or branched $(C_1\text{–}C_6)$alkyl group, to yield compounds of formula (VIII):

(VIII)

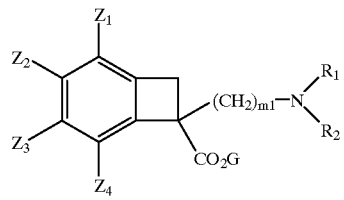

wherein $Z_1$, $Z_2$, $Z_3$, $Z_4$, $R_1$, $R_2$, G and m1 are as defined above, which compounds of formula (VIII) are treated with a dimagnesium compound of formula (IX):

$$Z'\text{—}Mg\text{—}CH_2\text{—}X\text{—}CH_2\text{—}Mg\text{—}Z' \quad (IX)$$

wherein X is as defined for formula (I) and Z' represents a halogen atom, to yield the compounds of formula (I/d), a particular case of the compounds of formula (I):

(I/d)

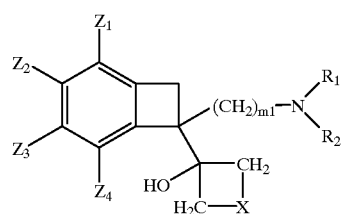

wherein $Z_1$, $Z_2$, $Z_3$, $Z_4$, $R_1$, $R_2$, X and m1 are as defined above, the totality of the compounds of formula (I/a) and formula (I/d), in the particular case where $R_1$ and $R_2$ simultaneously represent a hydrogen atom, constituting the compounds of formula (I/e):

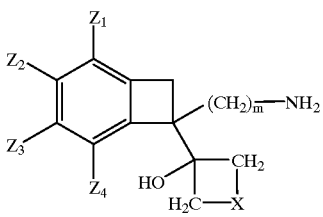

(I/e)

wherein $Z_1$, $Z_2$, $Z_3$, $Z_4$, X and m are as defined for formula (I), which compounds of formula (I/e) are:
→ either treated with 2-chloroethyl isocyanate in acetonitrile in the presence of triethylamine to yield the compounds of formula (I/f), a particular case of the compounds of formula (I):

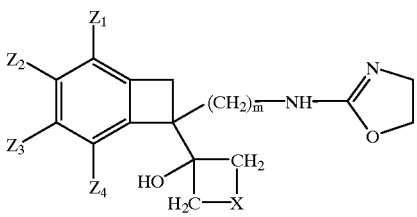

(I/f)

wherein $Z_1$, $Z_2$, $Z_3$, $Z_4$, X and m are as defined above,
→ or treated with imidazolin-2-ylsulphonic acid in the presence of an organic or mineral base in an alcohol or in acetonitrile to yield the compounds of formula (I/g), a particular case of the compounds of formula (I):

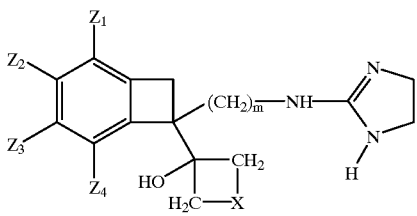

(I/g)

wherein $Z_1$, $Z_2$, $Z_3$, $Z_4$, X and m are as defined above,
which compounds (I/a) to (I/g) constitute the totality of the compounds of the invention, which are purified, if necessary, according to a conventional purification technique, which may be separated, if desired, into their various isomers according to a conventional separation technique, and which are converted, where appropriate, into addition salts thereof with a pharmaceutically acceptable acid.

The starting materials of formula II and IV are either known products or products obtained from known substances according to known processes.

The present invention relates also to pharmaceutical compositions comprising as active ingredient at least one compound of formula (I), its optical isomers or an addition salt thereof with a pharmaceutically acceptable acid, on its own or in combination with one or more inert, non-toxic, pharmaceutically acceptable excipients or carriers.

Among the pharmaceutical compositions according to the invention there may be mentioned more especially those that are suitable for oral, parenteral (intravenous, intramuscular or subcutaneous), per- or trans-cutaneous, nasal, rectal, perlingual, ocular or respiratory administration, and especially sublingual tablets, sachets, gelatin capsules, lozenges, suppositories, creams, ointments, dermal gels, injectable or drinkable preparations, aerosols, eye or nose drops, etc.

The useful dosage varies according to the age and weight of the patient, the route of administration, the nature and severity of the disorder, and whether any other treatments are being taken, and ranges from 0.5 to 25 mg of active ingredient, from one to three times per day.

The following Examples, given by way of non-limiting example, illustrate the present invention.

The melting points were determined using a Kofler hot-plate (K), or a hot-plate under a microscope (MK).

The starting materials used are known products or products prepared according to known procedures.

EXAMPLE 1

1-(N,N-Dimethylaminomethyl)-1-(1-hydroxycyclohex-1-yl)benzocyclobutane and the hydrochloride thereof Step A: 1-Cyano-1-(1-hydroxycyclohex-1-yl)benzocyclobutane Whilst maintaining the temperature at −78° C., 69 ml of 1.6M butyllithium in n-hexane are added to a solution of 12.9 g of 1-cyanobenzocyclobutane in 200 ml of tetrahydrofuran. After stirring for half an hour at that temperature, 15.5 ml of cyclohexanone are added and the reaction mixture is brought back to room temperature. After stirring for 3 hours at room temperature, the reaction mixture is hydrolysed at −10° C. with water. After extraction with diethyl ether, the organic phase is washed with brine, dried over $MgSO_4$ and concentrated in vacuo. The crystalline residue is recrystallised from isopropyl ether to yield 12.32 g of the desired product.

Melting point (K): 109–110° C.

Step B: 1-Aminomethyl-1-(1-hydroxycyclohex-1-yl)benzocyclobutane 0.7 g (18.55 mM) of $LiAlH_4$ is suspended in 38 ml of ether. The suspension is cooled to 0° C., and then a solution of 1.72 g (7.58 mM) of the product obtained in Step A in 38 ml of tetrahydrofuran is poured in whilst maintaining the temperature at from 0 to 5° C. After half an hour at that temperature, the reaction mixture is stirred for 3 hours at room temperature and then hydrolysed with 1 ml of water, 3 ml of 20% sodium hydroxide solution and again with 4 ml of water. Filtration and concentration are carried out to obtain 1.74 g of the expected product.

Step C: 1-(N,N-Dimethylaminomethyl)-1-(1-hydroxycyclohex-1-yl)benzocyclobutane hydrochloride 0.5 g (2.16 mM) of the product obtained in Step B is dissolved in 40 ml of $CH_3CN$. The suspension is cooled to 0° C. 0.3 g (4.33 mM) of sodium cyanoborohydride is then added, followed by 1 ml (11 mM) of 37% formaldehyde in water. Stirring is carried out for 2 hours at room temperature, and then the same quantities of sodium cyanoborohydride and formaldehyde are added and stirring is carried out again for 18 hours at room temperature. Hydrolysis is carried out with 5 ml of 1N HCl and, after 1 hour of contact, the mixture is diluted with distilled water, washed with ether and rendered basic with normal sodium hydroxide solution. Extraction, drying and evaporation yield 0.5 g of the desired product, which is converted into the hydrochloride thereof by the addition of a solution of ethereal hydrogen chloride. Recrystallisation from acetonitrile yields 0.45 g of the desired product.

Melting point (M.K.): 234–235° C.

EXAMPLE 2

1-(N,N-Dimethylaminomethyl)-1-(1-hydroxycyclohex-1-yl)-4,5-dimethoxybenzocyclobutane and the hydrochloride thereof The procedure is as for Example 1 using 1-cyano-4,5-dimethoxybenzocyclobutane as substrate in Step A.

Melting point (M.K.): 201–203° C.

EXAMPLE 3

1-(N,N-Dimethylaminomethyl)-1-(1-hydroxycyclohex-1-yl)-5-methoxybenzocyclobutane and the hydrochloride thereof The procedure is as for Example 1 using 1-cyano-5-methoxybenzocyclobutane as substrate in Step A.

Melting point (M.K.): 225–227° C.

EXAMPLE 4

1-(N,N-Dimethylaminomethyl)-1-(1-hydroxycyclohex-1-yl)-4-methoxybenzocyclobutane and the hydrochloride thereof The procedure is as for Example 1 using 1-cyano-4-methoxybenzocyclobutane as substrate in Step A.

Melting point (M.K.): 195–199° C.

EXAMPLE 5

1-(Aminomethyl)-1-(1-hydroxycyclohex-1-yl)-4-methoxybenzocyclobutane and the hydrochloride thereof The procedure is as for Example 1, Steps A and B using 1-cyano-4-methoxybenzocyclobutane as substrate in Step A.

Melting point (M.K.): 206–209° C.

EXAMPLE 6

1-(N,N-Methylaminomethyl)-1-(1-hydroxycyclohex-1-yl)-5-methoxybenzocyclobutane and the hydrochloride thereof Step D: 1-(Aminomethyl)-1-(1-hydroxycyclohex-1-yl)-5-methoxybenzocyclobutane The procedure is as for Step B of Example 1 using 1-cyano-1-(1-hydroxycyclohex-1-yl)-5-methoxybenzocyclobutane as starting material.

Step E: Ethyl N-{(1-hydroxycyclohex-1-yl-5-methoxybenzocyclobutan-1-yl)methyl}-carbamate A solution of 2 g (7.65 mM) of the compound obtained in Step D and 2.6 ml (19.8 mM) of triethylamine in 100 ml of methylene chloride is poured into a solution, cooled to 0° C., of 0.61 ml (7.65 mM) of ethyl chloroformate in 50 ml of methylene chloride. Stirring is carried out for 24 hours at room temperature, and the mixture is siluted with water and extracted with methylene chloride. The organic phases are washed first with 1N HCl and then with water until neutral and finally dried over $MgSO_4$ to yield, after evaporation, 2.2 g of the expected product.

Step F: 1-(N-Methylaminomethyl)-1-(1-hydroxycyclohex-1-yl)-5-methoxybenzocyclobutane hydrochloride A solution of 2.2 g (6.6 mM) of the product obtained in Step E in 50 ml of tetrahydrofuran is introduced dropwise into a suspension of 376 mg of $LiAlH_4$ (9.9 mM) in 40 ml of tetrahydrofuran. The mixture is refluxed for 3 hours, and is then left overnight at room temperature. After hydrolysis with 0.26 ml of water, 0.2 ml of sodium hydroxide solution and 0.94 ml of water, filtration and evaporation to dryness are carried out to obtain 1.8 g of the expected product, which is converted into the hydrochloride by the addition of ethereal hydrogen chloride.

Melting point (M.K.): 199–206° C.

EXAMPLE 7

(+)-Isomer of 1-(N,N-dimethyaminomethyl)-1-(1-hydroxycyclohex-1-yl)-5-methoxybenzocyclobutane and the hydrochloride thereof 2 g of the compound of Example 3 are subjected to high-performance chromatography (H.P.L.C.) on a chiral column of the CHIRALCEL OD® type, the mobile phase being composed of n-heptane/isopropanol/diethylamine in the proportions 1000/25/1. The first compound eluted corresponds to the title product with an enantiomeric excess of 99%, which compound is converted into the hydrochloride by the action of ethereal hydrogen chloride.

Melting point (M.K.): 228–232° C.

| $[\alpha]^{25° C.}$ (c = 1% in $CH_3OH$) | |
| --- | --- |
| λ(nm) | α |
| 589 | +16.5 |
| 578 | +17.2 |
| 546 | +19.7 |
| 436 | +35.9 |
| 365 | +61.5 |

EXAMPLE 8

(−)-Isomer of 1-(N,N-dimethylaminomethyl)-1-(1-hydroxycyclohex-1-yl)-5-methoxybenzocyclobutane and the hydrochloride thereof The second compound separated out during the chromatography carried out in Example 7 corresponds to the title product with an enantiomeric excess of 99%, which compound is converted into the hydrochloride thereof.

Melting point (M.K.): 228–232° C.

| $[\alpha]^{25° C.}$ (c = 1% in $CH_3OH$) | |
| --- | --- |
| λ(nm) | α |
| 589 | −16.6 |
| 578 | −17.3 |
| 546 | −20.0 |
| 436 | −36.7 |
| 365 | −63.3 |

EXAMPLE 9

1-(N,N-Dimethylaminomethyl)-1-(1-hydroxycyclohex-1-yl)-6-methoxybenzocyclobutane Step G: 6-Methoxybenzocyclobutan-1-ol 13.21 g (0.35 mol) of sodium borohydride are added in small fractions to a solution, maintained at 0° C., of 42.8 g (0.29 mol) of 6-methoxybenzocyclobutan-1-one in 1.5 liters of methanol. The temperature is maintained at 0° C. for 2 hours. After returning to room temperature, the reaction mixture is evaporated to dryness and then taken up in water. The aqueous phase is extracted several times with ethyl acetate. The organic phases are combined, washed with brine, dried over $MgSO_4$, filtered and evaporated to yield, after chromatography on silica, 29.2 g of the expected product in the form of a solid, the melting point of which is 71–73° C.

Step H: 1-Bromo-6-methoxybenzocyclobutane 13.5 ml (0.144 mol) of phosphorus tribromide are poured slowly into a solution of 29.1 g (0.194 mol) of the product obtained in the preceding Step in 940 ml of $NaHCO_3$ at 0° C. The mixture is maintained at that temperature for 20 minutes and then hydrolysed with 900 ml of $NaHCO_3$ at 0° C. The aqueous phase is extracted several times with ether. The combined ethereal phases are washed with water, dried over $MgSO_4$, filtered and evaporated to yield 23.1 g of yellow oil which corresponds to the structure of the expected product.

Step I: 1-Cyano-6-methoxybenzocyclobutane 10.5 g (0.16 mol) of potassium cyanide are added rapidly to a solution of 22.9 g (0.1 mol) of the product obtained in the preceding Step in 240 ml of dimethyl sulphoxide. The mixture is then heated at 55° C. for 4 hours. After returning to room temperature, the reaction mixture is poured into two liters of water. The aqueous phase is extracted several times with ether. The organic phases are washed with water, dried over $MgSO_4$, filtered and evaporated. The residue is chromatographed on silica (eluant $CH_2Cl_2$/cyclohexane: 50/50) to yield 10.4 g of the expected product, which melts at 58–59° C.

Step J: 1-Cyano-1-(1-hydroxycyclohex-1-yl)-6-methoxybenzocyclobutane

The procedure is as for Step A of Example 1 using the product obtained in Step I as substrate.

Melting point (K.): 116–120° C.

Step K: 1-Aminomethyl-1-(1-hydroxycyclohex-1-yl)-6-methoxybenzocyclobutane

The procedure is as for Step B of Example 1 using the product obtained in Step J as substrate.

Melting point (K.): 90–92° C.

Step L: 1-(N,N-Dimethylaminomethyl)-1-(1-hydroxycyclohex-1-yl)-6-methoxybenzocyclobutane The procedure is as for Step C of Example 1, starting from the compound obtained in Step K.

Melting point (M.K.): 125–133° C.

EXAMPLE 10

1-(N,N-Dimethylaminomethyl)-1-(4-hydroxytetrahydro-4H-pyran-4-yl)-4-methoxybenzocyclobutane The procedure is as for Example 1 using 1-cyano-4-methoxybenzocyclobutane and tetrahydro-4H-pyran-4-one, respectively, as substrates in Step A.

Melting point (K.): 88–90° C. (free base)

EXAMPLE 11

(+)-1-(N,N-Dimethylaminomethyl)-1-(1-hydroxycyclohex-1-yl)-4-methoxybenzocyclobutane hydrochloride 2 g of the compound of Example 4 are separated on a chiral column of the CHIRALCEL OD® type of H.P.L.C., the mobile phase being composed of n-heptane/isopropanol/$CF_3CO_2H$ in the proportions 1000/30/1. The first compound eluted corresponds to the expected product with an enantiomeric excess of 99.5%, which compound is converted into the hydrochloride by the action of ethereal hydrogen chloride.

Melting point (M.K.): 194–206° C.

| $[\alpha]^{25°\,C.}$ (c = 1% in $CH_3OH$) | |
|---|---|
| λ(nm) | α |
| 578 | +0.98 |
| 546 | +1.33 |
| 436 | +4.78 |

EXAMPLE 12

(−)-1-(N,N-Dimethylaminomethyl)-1-(1-hydroxycyclohex-1-yl)-4-methoxybenzocyclobutane hydrochloride The second compound separated out during the chromatography carried out in Example 11 corresponds to the expected product with an enantiomeric excess of 99%. It is converted into the hydrochloride by ethereal hydrogen chloride.

Melting point (M.K.): 210–212° C.

| $[\alpha]^{25°\,C.}$ (c = 1% in $CH_3OH$) | |
|---|---|
| λ(nm) | α |
| 578 | −1.32 |
| 546 | −1.6 |
| 436 | −5.94 |

EXAMPLE 13

1-(N,N-Dimethylaminomethyl)-1-(1-hydroxycyclohex-1-yl)-4-methoxy-5-chlorobenzocyclobutane hydrochloride The procedure is as for Example 1 using 5-chloro-1-cyano-4-methoxybenzocyclobutane as substrate in Step A.

Melting point (M.K.): 230–235° C.

EXAMPLE 14

1-(N,N-Dimethylaminomethyl)-1-(1-hydroxycyclohex-1-yl)-3-fluorobenzocyclobutane hydrochloride The procedure is as for Example 1 using 1-cyano-3-fluorobenzocyclobutane as substrate in Step A.

Melting point (M.K.): 240–245° C.

EXAMPLE 15

1-(N,N-Dimethylaminomethyl)-1-(1-hydroxycyclohex-1-yl)-3-chlorobenzocyclobutane hydrochloride The procedure is as for Example 1 using 3-chloro-1-cyanobenzocyclobutane as substrate in Step A.

Melting point (M.K.): 242–245° C.

EXAMPLE 16

1-(N,N-Dimethylaminomethyl)-1-(4-hydroxytetrahydro-4H-thiopyran-4-yl)-5-methoxybenzocyclobutane The procedure is as for Example 1 using 1-cyano-5-methoxybenzocyclobutane and tetrahdyro-4H-thiopyran-4-one, respectively, as substrate.

Melting point (M.K.): 118–123° C.

EXAMPLE 17

1-(N,N-Dimethylaminomethyl)-1-(1-hydroxycyclohex-1-yl)-4-trifluoromethylbenzocyclobutane hydrochloride The procedure is as for Example 1 using 1-cyano-4-trifluoromethylbenzocyclobutane as substrate in Step A.

Melting point (M.K.): 208–212° C.

EXAMPLE 18

1-(N,N-Dimethylaminomethyl)-1-(1-hydroxycyclohex-1-yl)-5-fluorobenzocyclobutane hydrochloride The procedure is as for Example 1 using 1-cyano-5-fluorobenzocyclobutane as substrate in Step A.

Melting point (M.K.): 233–238° C.

EXAMPLE 19

1-Aminomethyl-1-(1-hydroxycyclohex-1-yl)-4-hydroxybenzocyclobutane

The procedure is as for Example 1, Steps A and B, using 1-cyano-4-hydroxybenzocyclobutane as substrate in Step A.

Melting point (M.K.): 185–190° C.

EXAMPLE 20

1-(N,N-Dimethylaminomethyl)-1-(1-hydroxycyclohex-1-yl)-4-hydroxybenzocyclobutane The compound obtained in Example 19, treated according to the operating conditions described in Step C of Example 1, enables the expected product to be obtained.

Melting point (M.K.): 222–225° C.

EXAMPLE 21

1-Aminomethyl-1-(1-hydroxycyclohex-1-yl)-5-hydroxybenzocyclobutane

The procedure is as for Example 19 using 1-cyano-5-hydroxybenzocyclobutane as starting substrate.

Melting point (M.K.): 185–190° C.

EXAMPLE 22

1-(N,N-Dimethylaminomethyl)-1-(1-hydroxycyclohex-1-yl)-5-hydroxybenzocyclobutane The compound obtained in Example 21, treated according to the operating conditions described in Step C of Example 1, enables the expected product to be obtained.

Melting point (M.K.): 177–182° C.

EXAMPLE 23

1-(N,N-Dimethylaminomethyl)-1-(1-hydroxycyclohex-1-yl)-4,5-dichlorobenzocyclobutane The procedure is as for Example 1 using 4,5-dichloro-1-cyanobenzocyclobutane as substrate in Step A.

Melting point (M.K.): 135–137° C.

EXAMPLE 24

1-(N,N-Dimethylaminomethyl)-1-(1-hydroxycyclohex-1-yl)-6-chlorobenzocyclobutane hydrochloride The procedure is as for Example 1 using 1-cyano-6-chlorobenzocyclobutane as substrate in Step A.

Melting point (M.K.): 195–205° C.

EXAMPLE 25

1-(N,N-Dimethylaminomethyl)-1-(4-tert-butyl-1-hydroxycyclohex-1-yl)-5-methoxybenzocyclobutane hydrochloride The procedure is as for Example 1 using 1-cyano-5-methoxybenzocyclobutane and 4-tert-butyl-cyclohexanone, respectively, as substrate in Step A.

Melting point (M.K.): 206–220° C.

EXAMPLE 26

1-(N,N-Dimethylaminomethyl)-1-(4,4-dimethyl-1-hydroxycyclohex-1-yl)-5-methoxybenzocyclobutane hydrochloride The procedure is as for Example 1 using 1-cyano-5-methoxybenzocyclobutane and 4,4-dimethylcyclohexanone, respectively, as substrate in Step A.

Melting point (M.K.): 180–215° C. (sublimation at from 210 to 212° C.)

EXAMPLE 27

1-(N,N-Dimethylaminomethyl)-1-(1-hydroxy-4-selenocyclohex-1-yl)-5-methoxybenzocyclobutane The procedure is as for Example 1 using 1-cyano-5-methoxybenzocyclobutane and 4-selenocyclohexanone, respectively, as substrate in Step A.

Melting point (M.K.): 113–120° C.

EXAMPLE 28

1-(N,N-Dimethylaminomethyl)-1-(4-hydroxy-1-methyl-piperidin-4-yl)-5-methoxybenzocyclobutane The procedure is as for Example 1 using 1-cyano-5-methoxybenzocyclobutane and 1-methyl-4-piperidinone, respectively, as substrate in Step A.

Melting point (M.K.): 113–116° C.

EXAMPLE 29

1-(N,N-Dimethylaminomethyl)-1-(1-hydroxycyclohex-1-yl)-5-(trifluoromethylsulphonate)benzocyclobutane fumarate The procedure is as for Example 1 using 1-cyano-5-(trifluoromethylsulphonate)benzocyclobutane as substrate in Step A.

Melting point (M.K.): 72–77° C.

EXAMPLE 30

1-(N,N-Dimethylaminomethyl)-1-(1-hydroxycyclohex-1-yl)-6-bromobenzocyclobutane

The procedure is as for Example 1 using 1-cyano-6-bromobenzocyclobutane as substrate in Step A.

Melting point (M.K.): 196–200° C.

EXAMPLE 31

1-(N-Imidazolin-2-yl-aminomethyl)-1-(1-hydroxycyclohex-1-yl)-4-methoxybenzocyclobutane 2 g of the compound of Example 5 are dissolved in a solution containing 1.16 ml of triethylamine, 1.2 g of imidazolin-2-ylsulphonic acid and 16 ml of acetonitrile and the mixture is refluxed for 3 hours. The mixture is diluted with methylene chloride, washed with normal sodium hydroxide solution and then with water, dried over MgSO$_4$ and evaporated. Crystallisation from ether is carried out to obtain 600 mg of a solid which corresponds to the expected product.

EXAMPLE 32

1-[2-(N,N-Dimethylamino)ethyl]-1-(1-hydroxycyclohex-1-yl)-5-methoxybenzocyclobutane Step 1: 1-[2-(N,N-Dimethylamino)ethyl]-1-cyano-5-methoxybenzocyclobutane A solution of 10.5 ml of diisopropylamine in 55 ml of tetrahydrofuran is cooled to −78° C., and then 47 ml of a 1.6M solution of n-butyllithium in cyclohexane are added dropwise. Stirring is carried out for 15 minutes at −78° C. and then 10.8 g of 2-chloroethyldimethylamine hydrochloride are added rapidly. Stirring is carried out for 30 minutes at −78° C.

There is also prepared in a second three-necked flask a solution, cooled to −25° C., of 8.8 ml of diisopropylamine in 75 ml of tetrahydrofuran. 39.2 ml of a 1.6M solution of n-butyllithium in cyclohexane are added to that solution. After 15 minutes at −25° C., a solution of 10 g of 1-cyano-5-methoxybenzocyclobutane in 75 ml of tetrahydrofuran is added to the reaction mixture. Stirring is carried out for 30 minutes at −25° C.

Using a cannula, the first solution is transferred into the second at −78° C. Stirring is carried out at −78° C. for 1 hour and then the mixture is left overnight at room temperature. Hydrolysis is carried out at 0° C. with ammonium chloride. Extraction is carried out with ether, and the organic phase is dried over MgSO$_4$, filtered and evaporated to dryness. The residue obtained is taken up in 250 ml of HCl (1N) and washed with ether, and then the aqueous phase is adjusted to a pH of 12 with 20% sodium hydroxide solution. After extraction with methylene chloride and washing with water, the solution is dried over MgSO$_4$ and evaporated. 12.9 g of the expected product are obtained in the form of a pale yellow oil.

Step 2: 1-[2-(N,N-Dimethylamino)ethyl]-1-methoxycarbonyl-5-methoxybenzocyclobutane 6 g of the product obtained in the preceding Step are solubilised in 100 ml of methanol and 100 ml of methylene chloride. The solution is cooled to 0° C. and hydrogen chloride gas is bubbled in for 15 minutes. The mixture is left at room temperature for 3 days. After concentration under reduced pressure, the residue is solubilised in water and neutralised, with cooling, with a solution of 10% sodium hydrogen carbonate in water. Chromatography on silica gel (dichloromethane/methanol: 90/10) enables the expected product to be isolated.

Step 3: 1-[2-(N,N-Dimethylamino)ethyl]-1-(1-hydroxycyclohex-1-yl)-5-methoxybenzocyclobutane 5 g of the product obtained in the preceding Step dissolved in 50 ml of tetrahydrofuran are added slowly to 45.2 ml of a 0.5M solution of pentane-1,5-di(magnesium bromide) in tetrahydrofuran, whilst maintaining the temperature at 0° C. Stirring is carried out for 15 minutes at 0° C., and then for 1 hour at room temperature. The mixture is poured into an aqueous saturated ammonium chloride solution. Extraction is carried out with ether, and the extract is dried over magnesium sulphate, filtered and evaporated to dryness. Chromatography on silica gel (dichloromethane/ethanol: 90/10) enables the expected product to be isolated.

PHARMACOLOGICAL STUDY OF THE COMPOUNDS OF THE INVENTION

A. In vitro study

EXAMPLE 33

Determination of the affinity for serotonin reuptake sites

The affinity was determined by competitive experiments using [$^3$H]-paroxetine (NEN, Les Ulis, France). The membranes are prepared from frontal cortex of rate and are incubated in triplicate with 1.0 nM [$^3$H]-paroxetine and the cold ligand in a final volume of 0.4 ml, for 2 hours at 25° C. The incubation buffer contains 50 nM TRIS-HCl (pH 7.4), 120 mM NaCl and 5 mM KCl. The non-specific binding is determined using 10 μM citalopram. At the end of the incubation, the incubation medium is filtered and washed three times with 5 ml of cooled buffer. The radioactivity retained on the filters is determined by liquid scintillation counting. The binding isotherms are analysed by non-linear regression to determine the IC$_{50}$ values. Those values are converted into a dissociation constant (K$_i$) using the Cheng-Prusoff equation:

$$K_i = IC_{50}/(1+L/K_d)$$

wherein L is the concentration of [$^3$H]-paroxetine and K$_d$ is the dissociation constant of [$^3$H]-paroxetine for the serotonin reuptake site (0.13 nM). The results are expressed in pK$_i$ (−log K$_i$).

The compounds of the present invention demonstrate very good affinity for the serotonin reuptake sites. By way of example, the pK$_i$ of the compound of Example 8 is 8.7. By way of comparison, the pK$_i$ of fluoxetine in this test is 8.

EXAMPLE 34

Determination of the affinity for noradrenaline reuptake sites

The affinity was determined by competitive experiments using [$^3$H]-nisoxetine (Amersham, les Ulis, France). The membranes are prepared from frontal cortex of rat and are incubated in triplicate with 2 nM [$^3$H]-nisoxetine and the cold ligand in a final volume of 0.5 ml, for 4 hours at 4° C. The incubation buffer contains 50 mM TRIS-HCl (pH 7.4), 300 mM NaCl and 5 mM KCl. The non-specific binding is determined using 10 μM desipramine. At the end of the incubation, the incubation medium is filtered and washed three times with 5 ml of cooled filtration buffer (50 mM TRIS-HCl, pH 7.4, 300 mM NaCl and 5 mM KCl). the radioactivity retained on the filters is determined by liquid scintillation counting. The binding isotherms are analysed by non-linear regression to determine the IC$_{50}$ values. Those values are converted into a dissociation constant (K$_i$) using the Cheng-Prusoff equation:

$$K_i = IC_{50}/(1+L/K_d)$$

wherein L is the concentration of [$^3$H]-nisoxetine and K$_d$ is the dissociation constant of [$^3$H]-nisoxetine for the noradrenaline reuptake site (1.23 nM). The results are expressed in pKi (−log Ki).

By way of example, the compound of Example 9 has a pKi of 7.25.

B. In vivo study

EXAMPLE 35

Forced swimming test in the mouse (Porsolt et al., 1977)

The forced swimming test in the mouse consists of inducing a state of despair in the animal by placing it for 6 minutes in a cylinder full of water, from which it cannot escape. The naive animal struggles vigorously for the first few minutes and then adopts an immobile posture for the last few minutes of the test. Antidepressant products reduce the duration of immobility of the animal during the test.

the animals are male CD (IFFA-CREDO) mice (22–26 g) which, on the day before the test, are placed individually in transparent plastic cages (25×15×14 cm) on sawdust, with food and drink as desired. On the day of the test, 30 minutes after treatment (product or solvent, administered subcutaneously), each mouse is plunged for 6 minutes (T0–T6)

in a glass cylinder (23.5 cm in height, 11.5 cm in diameter) filled to a height of 6 centimeters with water maintained at 24±0.5° C. The total duration of immobility (sec.) of the animal during the last 4 minutes of the test (T2–T6) is observed: a mouse is considered to be immobile when it is floating in the water, making only small movements to keep its head out of the water.

The differences between the treated groups (product) and the control group (solvent) are evaluated statistically by variance analysis followed by Dunnett's test wherein $p<0.05$.

By way of example and to illustrate the effects of the compounds of the invention, the results for the compound of Example 4 are given in the following Table.

| Treatment | Doses mg/kg s.c. | Duration of immobility (sec.) | %/control | N |
|---|---|---|---|---|
| Control solvent | | 167.1 ± 16.1 | | 6 |
| Compound of | 0.63 | 157.3 ± 18.9 | 94 | 3 |
| Example 4 | 2.5 | 101.6 ± 57.3 | 61 | 3 |
| | 10.0 | 6.1 ± 6.1* | 4 | 4 |
| Control solvent | | 173.6 ± 10.1 | | 12 |
| fluoxetine | 2.5 | 163.5 ± 33.4 | 94 | 5 |
| | 10.0 | 130.5 ± 23.5 | 75 | 7 |
| | 40.0 | 127.1 ± 25.2 | 73 | 8 |

*$p < 0.05$

EXAMPLE 36

Suspension-by-the-tail test in the mouse

In this variation of the forced swimming test, the state of despair is induced in the mouse by suspending it head down by its tail. Placed in that uncomfortable situation, the animal struggles vigorously to start with and then adopts an immobile posture. Antidepressant products reduce the duration of immobility of the animal.

The animals are male NMRI (IFFA-CREDO) mice (22–26 g) which are housed, in groups of 20, in transparent plastic cages (59×38×20 cm) on sawdust, with food and drink as desired. On the day of the test, each mouse is placed in a separate cage as soon as it has been treated (subcutaneously) with the product or the solvent. Thirty minutes later, the animal is suspended by the tail from a hook using an adhesive tape attached to the tail. The hook is connected to a tension sensor which transmits all the animal's movements to a central processor (ITEMATIC-TST 1 system, ITEM-LABO, France). The total duration (sec.) of immobility of the animal during the 6 minutes of the test is recorded automatically.

The differences in the duration of immobility between the treated groups (product) and the control group (solvent) are analysed statistically by ANOVA followed by Dunnett's test, wherein $p<0.05$.

By way of example and to illustrate the effects of the compounds of the invention, the results for the compound of Example 3 are shown in the Table below.

| Treatment | Doses mg/kg s.c. | Immobility (sec.) | %/control | N |
|---|---|---|---|---|
| Control solvent | 0 | 80.3 ± 14.3 | | 12 |
| Compound of | 0.63 | 70.4 ± 13.5 | 88 | 8 |
| Example 3 | 2.5 | 41.1 ± 9.6 | 51 | 8 |
| | 10.0 | 27.8 ± 9.6* | 35 | 8 |
| Control solvent | | 76.6 ± 11.3 | | 17 |
| fluoxetine | 40.0 | 69.9 ± 17.8 | 91 | 10 |
| | 80.0 | 84.3 ± 12.4 | 110 | 10 |

*$p < 0.05$.

The results in the tests above illustrate the excellent activity of the compounds of the invention, especially in comparison with the reference compound.

What is claimed is:

1. A compound selected from those of formula (I):

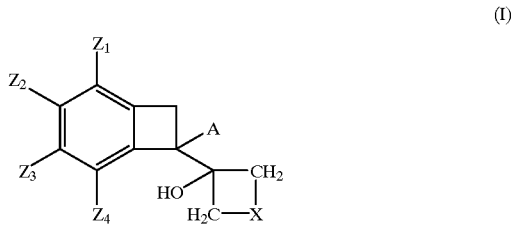

(I)

wherein:

$Z_1$, $Z_2$, $Z_3$ and $Z_4$, which may be identical or different, each represents hydrogen, halogen, linear or branched ($C_1$–$C_6$)alkyl, linear or branched ($C_2$–$C_6$)alkenyl, linear or branched ($C_2$–$C_6$)alkynyl, ($C_3$–$C_8$)-cycloalkyl-($C_1$–$C_6$)alkyl the alkyl moiety of which is linear or branched, hydroxy, linear or branched ($C_1$–$C_6$)alkoxy, benzyloxy-($C_2$–$C_6$)-alkenyloxy, the alkenyl moiety of which is linear or branched, linear or branched ($C_2$–$C_6$) alkynyloxy, cyano, trifluoromethyl, trifluoromethoxy, nitro, a group of formula —$OSO_2CF_3$, $OSO_2CH_3$, —$NHCOCH_3$, —$NHCOCF_3$, —$NHSO_2CH_3$,

or a group of formula

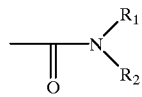

wherein $R_1$ and $R_2$, which may be identical or different, each represents hydrogen, linear or branched ($C_1$–$C_6$)alkyl, linear or branched ($C_2$–$C_6$)alkenyl, linear or branched ($C_2$–$C_6$)alkynyl, aryl-($C_1$–$C_6$)alkyl, the alkyl moiety of which is linear or branched, or ($C_3$–$C_8$)cycloalkyl-($C_1$–$C_6$)alkyl the alkyl moiety of which is linear or branched, X represents:
oxygen,
$S(O)_p$ wherein p represents 0 to 2 inclusive,
—$(CH_2)_n$ wherein n represents 1 to 4 inclusive,
or —$CH_2$—Y—$CH_2$— wherein Y represents oxygen, selenium,

wherein p is as defined above,

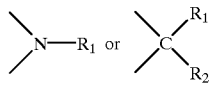

wherein $R_1$ and $R_2$ are as defined above,
A represents:

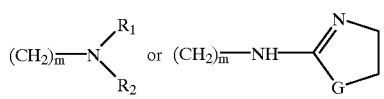

wherein
  $R_1$ and $R_2$ are as defined above,
  m represents 1 to 6 inclusive, and
  G represents oxygen or NH,
its isomers and pharmaceutically acceptable acid addition salts thereof.

2. A compound of claim 1 wherein A represents

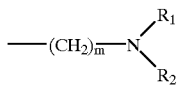

wherein m, $R_1$ and $R_2$ are as defined in claim 1, its isomers and pharmaceutically acceptable acid addition salts thereof.

3. A compound of claim 1 characterised in that X represents —$(CH_2)_n$— wherein n is as defined in claim 1, its isomers and pharmaceutically acceptable acid addition salts thereof.

4. A compound of claim 1, wherein:
A represents

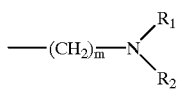

wherein $R_1$ and $R_2$ are as defined in claim 1 and m is 1,
and X represents —$(CH_2)_n$— wherein n is 3,
its isomers and pharmaceutically acceptable acid addition salts thereof.

5. A compound of claim 1, wherein X represents —$CH_2$—Y—$CH_2$— wherein Y is as defined in claim 1, its isomers and with a pharmaceutically acceptable acid addition salts thereof.

6. A compound of claim 1 which is 1-(N,N-dimethylaminomethyl)-1-(1-hydroxycyclohex-1-yl)-5-methoxybenzocyclobutane, and its pharmaceutically-acceptable acid addition salts.

7. A compound of claim 1 which is 1-(N,N-dimethylaminomethyl)-1-(1-hydroxycyclohex-1-yl)-4-methoxybenzocyclobutane, and its pharmaceutically-acceptable acid addition salts.

8. A compound of claim 1 which is (−)-1-(N,N-dimethylaminomethyl)-1-(1-hydroxycyclohex-1-yl)-5-methoxybenzocyclobutane, and its pharmaceutically-acceptable acid addition salts.

9. A method for treating a living body afflicted with depression, panic attacks, obsessive compulsive disorders, phobias, impulsive disorders, drug abuse or anxiety, comprising the step of administering to the living body an amount of a compound of claim 1 which is effective for alleviation of said condition.

10. A pharmaceutical composition useful in treatment of depression comprising as active principle an effective amount of a compound as claimed in claim 1, in combination with one or more pharmaceutically-acceptable excipients or carriers.

11. A method for treating a living body afflicted with depression, panic attacks, obsessive compulsive disorders, phobias, impulsive disorders, drug abuse or anxiety, comprising the step of administering to the living body an amount of a compound of claim 2 which is effective for alleviation of said condition.

12. A pharmaceutical composition useful in treatment of depression comprising as active principle an effective amount of a compound as claimed in claim 2, in combination with one or more pharmaceutically-acceptable excipients or carriers.

13. A method for treating a living body afflicted with depression, panic attacks, obsessive compulsive disorders, phobias, impulsive disorders, drug abuse or anxiety, comprising the step of administering to the living body an amount of a compound of claim 3 which is effective for alleviation of said condition.

14. A pharmaceutical composition useful in treatment of depression comprising as active principle an effective amount of a compound as claimed in claim 3, in combination with one or more pharmaceutically-acceptable excipients or carriers.

15. A method for treating a living body afflicted with depression, panic attacks, obsessive compulsive disorders, phobias, impulsive disorders, drug abuse or anxiety, comprising the step of administering to the living body an amount of a compound of claim 4 which is effective for alleviation of said condition.

16. A pharmaceutical composition useful in treatment of depression comprising as active principle an effective amount of a compound as claimed in claim 4, in combination with one or more pharmaceutically-acceptable excipients or carriers.

17. A method for treating a living body afflicted with depression, panic attacks, obsessive compulsive disorders, phobias, impulsive disorders, drug abuse or anxiety, comprising the step of administering to the living body an amount of a compound of claim 5 which is effective for alleviation of said condition.

18. A pharmaceutical composition useful in treatment of depression comprising as active principle an effective amount of a compound as claimed in claim 5, in combination with one or more pharmaceutically-acceptable excipients or carriers.

* * * * *

UNITED STATES PATENT AND TRADEMARK OFFICE
CERTIFICATE OF CORRECTION

PATENT NO. : 6,107,345
DATED : August 22, 2000
INVENTOR(S) : J.L. Peglion, A. Dessinges, J.C. Harmange, M. Millan, A. N. Tancredi, M. Brocco It is certified that error appears in the above-identified patent and that said Letters Patent is hereby corrected as shown below:

Column 3,
Line 4: "comphoric" should read: -- camphoric --.
Line 20: "formula (K)" should read: -- formula (I) --.

Column 8,
Line 39: "(18.55 mM)" should read: -- (18.44 mM) --.

Column 9,
Line 37: "1- (N,N-" should read: -- 1- (N- --.
Line 53: "siluted" should read: -- diluted --.

Column 18,
Line 38 (approx): Insert the word -- the -- after "alkynyloxy".

Column 19,
Line 55: Delete "with a".

Signed and Sealed this

Twenty-first Day of August, 2001

Attest:

NICHOLAS P. GODICI
Attesting Officer  Acting Director of the United States Patent and Trademark Office